United States Patent [19]

Mihailovski

[11] 4,071,545

[45] Jan. 31, 1978

[54] PREPARATION OF S-TRICYCLOHEXYLTIN-O,O-DIISOPROPYL DITHIOPHOSPHATE

[75] Inventor: Alexander Mihailovski, Kensington, Calif.

[73] Assignee: Stauffer Chemical Company, Westport, Conn.

[21] Appl. No.: 674,257

[22] Filed: Apr. 6, 1976

Related U.S. Application Data

[63] Continuation-in-part of Ser. No. 619,136, Oct. 2, 1975, abandoned.

[51] Int. Cl.$^2$ .............................................. C07F 7/22
[52] U.S. Cl. .................................................. 260/429.7
[58] Field of Search ...................................... 260/429.7

[56] References Cited

U.S. PATENT DOCUMENTS

| 2,382,775 | 8/1945 | Cook | 260/987 X |
| 2,786,812 | 3/1957 | McDermott | 260/429.7 X |
| 3,358,006 | 12/1967 | Walsh et al. | 260/429.7 |
| 3,542,825 | 11/1970 | Hoye | 260/429.7 |

FOREIGN PATENT DOCUMENTS

| 1,163,738 | 9/1969 | United Kingdom. |
| 1,349,916 | 4/1974 | United Kingdom. |

OTHER PUBLICATIONS

Chemical Abstracts, V63,7032b, (1965).
Chemical Abstracts, V50,9010f, (1956).
Chemical Abstracts, V70,78100x, (1969).

Primary Examiner—Helen M. S. Sneed
Attorney, Agent, or Firm—Joel G. Ackerman

[57] ABSTRACT

S-tricyclohexyltin-O,O-diisopropyl dithiophosphate, a useful miticide, is produced by reaction of tricyclohexyltin chloride with diisopropyl dithiophosphoric acid and a base selected from the group consisting of alkali metal hydroxides and ammonium hydroxide in a two-phase aqueous-organic system. The reaction may be conducted with or without the use of a solvent. In the case of strong alkali metal hydroxides such as sodium hydroxide the reaction is preferably conducted at a pH of about 7 or less.

9 Claims, No Drawings

PREPARATION OF S-TRICYCLOHEXYLTIN-O,O-DIISOPROPYL DITHIOPHOSPHATE

CROSS-REFERENCE TO RELATED APPLICATION

This application is a continuation-in-part of Application Ser. No. 619,136, filed Oct. 2, 1975 now abandoned.

BACKGROUND AND PRIOR ART

This application relates to an improved process for the production of S-tricyclohexyltin-O,O-diisopropyl dithiophosphate. This compound is disclosed in British Patent No. 1,349,916 as being a useful miticide and insecticide.

As disclosed in Example 1 of the British patent this compound was prepared by mixing tricyclohexyltin chloride with potassium diisopropyl dithiophosphate in acetone. Similar techniques were used in processes disclosed in U.S. Pat. Nos. 2,786,812, 3,358,006 and 3,542,825 and the article by Kubo et al., Agricultural and Biological Chemistry (Japan, 29, 43–55 (1965). The acetone and other similar solvents such as methyl ethyl ketone and lower aliphatic alcohols such as methanol and ethanol, were used in order to obtain a homogeneous reaction medium.

Potassium diisopropyl dithiophosphate is a relatively expensive reagent, whether it is first made and then isolated (similarly to the processes described in U.S. Pat. No. 3,358,006, for example), or purchased from a commercial source. Production and isolation of this salt, as in the above references, results in some yield loss, thus adding to its cost. The use of acetone or similar solvents as the reaction medium requires downstream equipment for separation of solvent, product and by-products and recycling of solvent to the main processing stages. The use of acetone also requires great care in downstream product recovery steps such as washing, to prevent formation of emulsions.

It would be advantageous to provide a process for the production of S-tricyclohexyltin-O,O-diisopropyl dithiophosphate in which it would not be necessary to utilize potassium diisopropyl dithiophosphate per se.

It would also be advantageous to provide a process for the production of S-tricyclohexyltin-O,O-diisopropyl dithiophosphate in which a solvent would not be necessary, as the cost of a solvent and of solvent recovery and recycling equipment could be saved. Additionally, if a solvent could be omitted from the process, the capacity of apparatus for the reaction could be improved, or smaller and therefore less expensive apparatus could be utilized for the same production capacity.

It would be advantageous to provide a process for production of maximum yields of S-tricyclohexyltin-O,O-diisopropyl dithiophosphate based on the intermediate tricyclohexyltin chloride.

The invention described herein, in its various embodiments, achieves some or all of the advantages stated above as well as other advantages which will be apparent from the description which follows.

SUMMARY OF THE INVENTION

The invention comprises a process for the production of S-tricyclohexyltin-O,O-diisopropyl dithiophosphate comprising reacting tricyclohexyltin chloride, diisopropyl dithiophosphoric acid and a base selected from the group consisting of alkali metal hydroxides and ammonium hydroxide in a substantially two-phase system comprising an aqueous phase and an organic phase.

In a preferred embodiment, the invention comprises conducting the above-mentioned process in the absence of an organic solvent.

DETAILED DESCRIPTION OF THE INVENTION

In general, the process of the present invention is carried out by the reaction of tricyclohexyltin chloride, diisopropyl dithiophosphoric acid and a base selected from the group consisting of alkali metal hydroxides and ammonium hydroxide in a two-phase aqueous-organic system. The alkali metal hydroxide may be any suitable alkali metal hydroxide such as potassium hydroxide, sodium hydroxide, etc.

The reaction can also be carried out in the presence of an organic solvent which is immiscible with water, such as toluene, benzene or xylene. However, the reaction is preferably carried out without the use of any organic solvent by conducting the reaction at a temperature at or above the melting point of the product S-tricyclohexyltin-O,O-diisopropyl dithiophosphate, which is about 30° C to 41° C.

In a preferred embodiment, therefore, an aqueous solution of the base, tricyclohexyltin chloride, and diisopropyl dithiophosphoric acid are reacted together at a temperature of about 40° C or somewhat greater, in the absence of an organic solvent. The system is a substantially two-phase one; the tricyclohexyltin chloride is a solid, insoluble in water, and forms the organic phase, along with the desired product, as mentioned below. The molten product, as it forms acts as a solvent for the solid tricyclohexyltin chloride. Operation in such a fashion further decreases the cost of the process since the cost of the solvent and the solvent reclaiming and recycling equipment is saved. Additionally, the equipment can be sized smaller as it will no longer be necessary to handle large quantities of solvent. Alternatively, using equipment of the same size a greater production capacity can be obtained.

In this embodiment the reaction temperature need not be very much above 40°–41° C. as the reaction between tricyclohexyltin chloride and the alkali metal salt of diisopropyl dithiophosphoric acid is very rapid; gas chromatographic monitoring shows that very shortly after initiation of the reaction, the tricyclohexyltin chloride is almost completely reacted. Since there is no need to operate at temperatures substantially in excess of the melting point of the product, a reasonably convenient upper limit would be about 80° C. However, this figure is not essential. Since the reaction proceeds very quickly the molten S-tricyclohexyltin-O,O-diisopropyl dithiophosphate is rapidly formed. This compound is denser than the aqueous medium involved and therefore is found in the lower (organic) layer. The product is thus readily recovered by simply separating it from the aqueous phase and drying, if necessary. The aqueous phase contains by-product sodium chloride, which can be disposed of by conventional means. As compared to the prior art process, therefore, the preparation of this product is not, and need not be, carried out in a homogeneous system.

It has been found that when a strong alkali such as sodium or potassium hydroxide is utilized, the pH of the aqueous phase should be kept at a maximum of about 7. At higher pHs, the tricyclohexyltin chloride begins to hydrolyze, forming the corresponding hydroxide or oxide as impurities and thus the yield and purity of the desired product is decreased. However, the excess of ammonium hydroxide can be used without affecting the product yield of quality.

The reaction between an alkali metal salt of diisopropyl dithiophosphoric acid and tricyclohexyltin chloride, though very rapid, is not exothermic. However, it was found that when utilizing ammonium hydroxide, the preferable reaction temperature is about 55° to about 65° C. Reaction time in general, is between about 0.5 and about 3 hours for all bases.

The reaction may also be carried out in the presence of an organic solvent. The solvent should be one which is at least substantially immiscible with water and from which the desired product can be readily separated. Toluene, for example, is a suitable solvent for this purpose, as are benzene and xylene. It has been found most advantageous to use a solvent:water ratio of at least 2:1 by volume; otherwise poor phase separation may occur. When using a solvent, reaction temperatures are essentially limited at the lower end by a temperature sufficiently above 0° C to prevent the aqueous phase from freezing and, at the upper end, by the boiling point of the solvent. A general temperature range would be between about 10° C and about 145° C, the boiling point of commercial xylene solvents. However, it is not necessary to operate at the boiling point of the solvent; to conserve energy, a reasonable temperature range would be between about 10° C and about 80° C.

In one embodiment of this invention, whether operating with or without an organic solvent, the reactants, and water, may be mixed together and reacted in one step. For instance, an aqueous solution of the alkali metal hydroxide may be mixed wth tricyclohexyltin chloride and diisopropyl dithiophosphoric acid in a one-step reaction, so long as, when a strong alkali is used, the pH of the aqueous phase is maintained at a maximum of about 7. Alternatively, for easier control of the pH, the aqueous phase may be first prepared by combining an aqueous solution of the base with diisopropyl dithiophosphoric acid, in effect forming the salt of the dithiophosphoric acid (in solution) and then combining the total aqueous phase with tricyclohexyltin chloride. The neutralization reaction between the acid and base may be exothermic, but the temperature can be allowed to climb without adversely affecting the subsequent reaction with tricyclohexyltin chloride.

An illustration of the invention there are prepared the following specific examples which are, however, not intended to limit the invention in any way. Example 1 illustrates the invention using sodium hydroxide as the alkali metal hydroxide and toluene as an organic solvent. Examples 2 and 3 illustrate preferred embodiments of the invention in which the reaction is conducted in the absence of an organic solvent respectively utilizing sodium hydroxide and ammonium hydroxide.

EXAMPLE 1

Into a two-liter round-bottom flask were introduced 214.5 g. (0.5 mole based on 94.1% purity) tricyclohexyltin chloride and 500 ml. toluene. In a separate one-liter flask immersed in an ice bath were mixed 128.6 g. (0.60 mole) diisopropyl dithiophosphoric acid and a solution of sodium hydroxide made from 48.0 g 50% sodium hydroxide (0.60 mole sodium hydroxide) and 250 ml. water. Additional acid was then added to reach a pH of 7.

The neutralized products were washed with toluene and the remaining aqueous solution was then mixed with the tricyclohexyltin chloride-toluene solution in the first flask. The temperature rose from 19° to 22° C. The mixture was stored at room temperature for 1 hour; the organic layer was separated and washed with water. Toluene was recovered by evaporation at 50° C under vacuum. 278.5 g. of product were obtained in the molten form and cooled. The purity was found to be 99.5%, and the yield based on starting tricyclohexyltin chloride was 95.3%.

EXAMPLE 2

Into a 500 ml, multi-neck, round bottom flask was placed 48.0 g (0.240 F.W. NaOH) 20% NaOH solution. To the base was then added slowly 59.1 g (0.240 mole) diisopropyl dithiophosphoric acid plus a small extra amount to reach pH 7. This neutralization was performed at 20°-25° C by immersing the flask in an ice bath. The aqueous solution was then heated to 60° C and 85.8 g (0.200 mole corrected for 94.1% purity) tricyclohexyltin chloride was added. The mobile, two-phase system was vigorously stirred and held at 60° C for 2 hours.

The aqueous phase was separated and the lower organic phase washed once with 50 ml warm water. To avoid mechanical losses all equipment was washed after the reaction with 25 ml toluene and this toluene wash was combined with the wet organic product. The toluene and water were evaporated for one hour at 50° C and 10 uHg. The product solidified on cooling to room temperature. Its weight was 114.7 g; m.p. 39°–41° C. Its purity was 93.0% and a yield corrected for reagent and product purity of 91.8% was realized.

EXAMPLE 3

To 40.3 g (0.10 mole) tricyclohexyltin chloride in a 500 ml flask was added a solution made from 100 ml water, 27.9 g. (0.13 mole) diisopropyl dithiophosphoric acid and 8.8 g. (0.15 mole) concentrated ammonium hydroxide. The mixture was heated at 55°-60° C for 3 hours. The product settled at the bottom of the flask and the product layer was dissolved in 100 ml toluene and washed 4 times with 50 ml portions of water. The solvent was removed by evaporation to give 51.9 g. of product with a purity of 94.0% and a yield of 89.2%.

What is claimed is:

1. A process for the production of S-tricyclohexyltin-O,O-diisopropyl dithiophosphate comprising reacting tricyclohexyltin chloride, diisopropyl dithiophosphoric acid and a base selected from the group consisting of alkali metal hydroxides and ammonium hydroxide in a substantially two-phase system comprising an aqueous phase and an organic phase.

2. A process according to claim 1 in which the reaction is carried out in the absence of an organic solvent.

3. A process according to claim 1 in which the reaction is carried out at a temperature at or above the melting point of S-tricyclohexyltin-O,O-diisopropyl dithiophosphate.

4. A process according to claim 1 in which the reaction is carried out in the presence of a substantially water-immiscible organic solvent.

5. A process according to claim 4 in which the solvent is toluene.

6. A process according to claim 1 in which the pH of the aqueous phase is maintained at a maximum of about 7.

7. A process according to claim 1 in which the base is sodium hydroxide.

8. A process according to claim 1 in which the base is ammonium hydroxide.

9. A process according to claim 1 further comprising recovering S-tricyclohexyltin-O,O-diisopropyl dithiophosphate from the reaction products.

* * * * *

UNITED STATES PATENT AND TRADEMARK OFFICE
CERTIFICATE OF CORRECTION

PATENT NO. : 4,071,545
DATED : January 31, 1978
INVENTOR(S) : Alexander Mihailovski It is certified that error appears in the above-identified patent and that said Letters Patent are hereby corrected as shown below:

In Column 2, at line 24, the number "30" should read --39--.

*Signed and Sealed this*

*Twentieth* Day of *June 1978*

[SEAL]

Attest:

RUTH C. MASON
*Attesting Officer*

DONALD W. BANNER
*Commissioner of Patents and Trademarks*